United States Patent [19]
Jolivet-Reynaud

[11] Patent Number: 5,985,541
[45] Date of Patent: Nov. 16, 1999

[54] PEPTIDE CAPABLE OF BEING RECOGNIZED BY ANTIBODIES RECOGNIZING THE C33 ANTIGEN OF HEPATITIS C VIRUS

[75] Inventor: Colette Jolivet-Reynaud, Bron, France

[73] Assignee: Bio Merieux, Marcy L'eoile, France

[21] Appl. No.: 08/687,219

[22] Filed: Jul. 25, 1996

[30] Foreign Application Priority Data

Jul. 25, 1995 [FR] France ................................. 95 09005

[51] Int. Cl.⁶ .......................... C12Q 1/70; G01N 33/543
[52] U.S. Cl. ............................. 435/5; 436/518; 530/328; 530/329; 530/413
[58] Field of Search .................................. 530/327, 328, 530/329, 330, 413; 435/5; 436/518

[56] References Cited

FOREIGN PATENT DOCUMENTS

WO 94/13700  6/1994  WIPO .
WO 95/00670  1/1995  WIPO .
WO 96/12810  5/1996  WIPO .

OTHER PUBLICATIONS

Y. Khudyakov et al., "Linear B–Cell Epitopes of the NS3–NS5 Proteins of the Hepatitis C Virus as Modeled with Synthetic Peptides", *Virology,* vol. 206, pp. 666–672 (1995).

J. Scott et al., "Search for Peptide Ligands with an Epitope Library", *Science,* vol. 249, pp. 386–390, Jul. 27, 1990.

Farci et al., "Lack of Protective Immunity Against Reinfection with Hepatitis C Virus", Science, 258:135–140, Oct. 2, 1992.

*Primary Examiner*—Donna C. Wortman
*Assistant Examiner*—Brenda G. Brumback
*Attorney, Agent, or Firm*—Oliff & Berridge, PLC

[57] ABSTRACT

Polypeptide able to react specifically with an antibody directed against the C33 antigen of hepatitis C virus, and that has a peptide sequence including all or part of the Asp-Gly-Ala-Lys-Phe-Ser-Ser-Arg-Leu-Gly-Ala-Ala-Gly-Ala SEQ ID NO: 1 sequence, or a sequence derived from this peptide sequence recognized by the antibody. This polypeptide has applications for detection of C33 antigen and anti-C33 antibodies.

19 Claims, No Drawings

PEPTIDE CAPABLE OF BEING RECOGNIZED BY ANTIBODIES RECOGNIZING THE C33 ANTIGEN OF HEPATITIS C VIRUS

FIELD OF THE INVENTION

The present invention relates to a polypeptide able to substitute for the C33 antigen of hepatitis C virus (HCV), a polynucleotide whose expression corresponds to said polypeptide, and their utilization for diagnostic and therapeutic purposes.

BACKGROUND OF THE INVENTION

The hepatitis C virus (HCV) is a single-stranded 9.4 Kb RNA virus recognized as the responsible agent for certain non-A, non-B forms of hepatitis. The viral genome of HCV codes for a polyprotein with approximately 3010 amino acids which, after translation, undergoes several maturing stages, leading to production of so-called structural proteins and of so-called non-structural (NS) proteins. The structural proteins of the HCV virus are the nucleocapsid proteins (corresponding to the C region of the HCV genome), the matrix protein (M), and two glycosylated envelope peptides, gp33 (E1) and gp72 (E2/NS1). The non-structural proteins are NS2 which is a protein bound to the viral membrane, NS3 which plays the roles of protease and helicase, and NS5 which corresponds to viral polymerase. The function of NS4 is still unknown. Clinical studies have shown that antibodies specifically directed against the preserved regions of the nucleocapsid and against NS3 appear early after HCV infection. Hence these two proteins are excellent markers for diagnostic tests of HCV infection. Other studies have shown the existence of several immunodominant antigens, particularly the C33 antigen of the NS3 region and more particularly the antigen noted C33c corresponding to a fraction of C33 (see WO 9115771). However, obtaining these peptides, one of which has 266, and the other, 93 amino acids in an isolated form by genetic recombination or chemical synthesis presents a number of obstacles linked in particular to post-translational modifications that are necessary for obtaining sufficiently immunoreactive peptides, or to difficulties involved in chemical synthesis of peptides of such length.

Surprisingly, the discovery has been made of a polypeptide synthesized chemically, or by genetic recombination methods, which has undergone no modification after its synthesis, which is capable of being recognized by antibodies specific to HCV infections, notably anti-HCV, while its sequence has no analogy with that of the C33 protein.

DEFINITIONS

Before discussing the objects according to the invention, a number of terms employed in the specification will be defined below.

"Polypeptide" designates a peptide or a protein consisting of an assemblage of amino acid residues linked by peptide bonds, and obtained by chemical synthesis or by genetic recombination techniques. When describing peptides, the expression "amino acid" is often employed to designate an amino acid residue present in the peptide. The polypeptides according to the invention can be obtained by classical synthesis methods, for example, in an automatic peptide synthesizer, or by genetic engineering, for example, inserting a DNA sequence that codes said polypeptide in an expression vector such as a plasmid or a virus, examples of which are described in the present application, transformation of cells with this expression vector, and culturing these cells. These cells can be eucaryotic or procaryotic.

"Sequence derived from another amino acid sequence" means an amino acid sequence modified by chemical modification of one or more amino acids, which is recognized by at least one anti-C33 antibody. Thus, "derived sequence" means, in particular, sequences in which one or more amino acids is/are replaced by one or more other amino acids, as illustrated in Example 5 hereinbelow; sequences in which one or more amino acids in the L series is replaced by an amino acid in the D series and vice-versa; sequences into which a modification of the amino acid side chains has been introduced, for example, acetylation of the amine functions, carboxylation of the thiol functions, esterification of the carboxylic functions; modification of the peptide bonds, such as by carba, retro, inverse, retro-inverse, reduced, and methylene-oxy bonds (see in particular PCT WO 94/05311).

"Sera of individuals or animals infected by HCV" here means sera of patients who have contracted an HCV infection and which contain immunoglobulins that specifically recognize at least the C33 antigen of the HCV virus.

"Immunologically compatible" means a substance compatible with the relevant immunological process(es).

"A predetermined quantity" means a quantity of the substance whose concentration is known or can be determined. The concentration can be expressed in any of various forms, including, for example, as moles/sample, an effective equivalent concentration, a concentration equal to or a diluted fraction of another quantity, reaction units and moles/liter. The quantity may be predetermined by means such as measuring an aliquot of a source sample, empirically determining a concentration or relative concentration, for example, by using a calibration curve or table, and/or by saturating a number of binding sites.

"Polynucleotide" means either a DNA sequence or an RNA sequence or a cDNA sequence resulting from inverse transcription of an RNA sequence of natural or synthetic origin, with or without modified bases.

The term "solid substrate" includes but is not limited to a microtitration slide, a foil, a cone, a well, a bead, or any appropriate microparticulate substrate, and includes all materials on which the peptide fragments of the invention can be immobilized. This substrate can be made of any appropriate material, particularly polysaccharides, such as cellulose materials, for example paper, cellulose derivatives such as nitrocellulose and cellulose acetate, polymers such as vinyl chloride, polyethylene, polystyrene, polyacrylate, or copolymers such as vinyl chloride and propylene copolymers, vinyl chloride and vinyl acetate copolymers, styrene-based copolymers, natural fibers such as cotton, and synthetic fibers such as nylon. Preferably, the solid substrate is a polystyrene polymer, a butadiene-styrene copolymer, or a butadiene-styrene copolymer mixed with one or more polymers or copolymers chosen from: polystyrene, styrene acrylonitrile or styrene methylmethacrylate copolymers, propylenes, polycarbonates, or the like.

Terms used herein are well understood in the art and are described in several references, for example, Maniatis, Cold Spring Harbor Laboratory Press, 2d edition, 1989, which is totally incorporated by reference.

SUMMARY OF THE INVENTION

The present invention relates to a polypeptide capable of reacting specifically with an anti-C33 antibody whose sequence includes all or part of SEQ ID NO: 1, or a derived sequence. The peptides according to the invention contain at least five, and preferably, at least six amino acids. Peptides may include an entire sequence as listed in the sequence listings or portions of said sequence with one and possibly two or three amino acids deleted from the N-terminal and/or C-terminal. Peptides not listed in the sequence listings, for example, derived sequences, are also embodiments of this invention.

The peptide sequence according to the invention contains all or part of the sequences SEQ ID NO: 2, SEQ ID NO: 3, SEQ ID NO: 4, SEQ ID NO: 5, SEQ ID NO: 6, SEQ ID NO: 7, SEQ ID NO: 8, and in particular, the sequence of said fragment corresponds to SEQ ID NO: 10, or corresponding derived sequences, such as SEQ ID NO: 9, and preferably, the sequences SEQ ID NO: 32 to SEQ ID NO: 37.

Thus, the invention relates in particular to peptide sequences chosen from the sequences of at least five (and preferably, at least six) consecutive amino acids present in the sequences indicated. Peptides of the invention can be synthesized and/or isolated by methods known in the art.

These polypeptides can be prepared by known methods.

Also, the polypeptides according to the invention can be conjugated according to techniques well known to the individual skilled in the art, to a carrier molecule (such as, for example, a natural or recombinant protein other than a natural or recombinant HCV antigen, a synthetic polymer of amino acids or of aliphatic chains, or a nucleic fragment) or a tracer molecule (such as, for example, an oligonucleotide or an enzyme such as horseradish peroxidase, an alkaline phosphatase, or a galactosidase) or a radioelement. The peptides according to the invention can also be attached to a substrate. The carrier molecule obviously should be unable to react or at least should be unreactive under the assay conditions with the anti-C33 antibodies.

A second object of the present invention is an application of a polypeptide described above, and consists of a reagent for detection of HCV infection, said reagent including, as its reactive substance, at least one polypeptide according to the invention.

A third object of the invention is a kit for detecting HCV infection, including the reagent described above, attached to a solid substrate that is immunologically compatible with said reagent.

The reagent can be attached to the solid substrate directly or indirectly.

By the direct method, two approaches are possible: either by adsorption of the reagent on the solid substrate, or by non-covalent bonds (principally of the hydrogen, Van der Wals, or ionic type), or by establishing covalent bonds between the reagent and the substrate. Indirectly, it is possible to pre-attach an "antireagent" compound (by adsorption or covalence) to the substrate, said compound being able to interact with the reagent such as to immobilize the system on the solid substrate.

The invention also relates to a method for detecting and/or separating and/or purifying and/or assaying any anti-C33 antibodies present in a sample, in which a peptide according to the invention is used to form an immune complex with said antibodies if they are present in the sample.

The invention relates in particular to a method for detecting and/or concentrating and/or separating and/or purifying and/or assaying anti-C33 antibodies in a sample of biological fluid, including the following steps: said sample is placed in contact with a reagent according to the invention under conditions permitting an immune reaction, then any immune complex formed is detected, possibly separated, and/or quantified.

The invention also relates to a method for assaying the HCV C33 antigen in a sample of biological fluid carried out by the competition technique: said sample is simultaneously placed in contact with a predetermined quantity of anti-C33 antibody and a predetermined quantity of a reagent according to the invention, and the quantity of C33 antigen in said sample is determined by deduction from the measured quantity of the complex formed between the reagent and said anti-C33 antibodies.

The invention also relates to a process according to the invention for assaying the C33 antigen in a sample of biological fluid, according to which, in a first step, said sample is placed in contact with a predetermined quantity of anti-C33 antibody and, in a second step, a predetermined quantity of a reagent according to the invention is added, and the quantity of C33 antigen in said sample is determined by deduction from the measured quantity of the complex formed between said reagent and said anti-C33 antibodies.

These processes are implemented in known fashion. They may be based on a radioimmunology method of the RIA, RIPA (radioimmunologic precipitation assay), or IRMA (immunoradiometric assay) type, or an immunoenzymatic method of the Western blot or ELISA type.

Another application of the polypeptides according to the invention is an active immunotherapeutic composition, particularly a vaccine preparation, which has, as an active agent, a polypeptide described above, said active agent possibly being in the conjugated form, and possibly a pharmaceutically-acceptable excipient. The conjugated form is well known and will not be discussed here.

The invention also offers a polynucleotide that codes for a polypeptide described above. The sequence of such a polynucleotide can of course vary, taking the degeneracy of the genetic code into account. This polynucleotide includes, for example, a nucleotide sequence such as the sequence SEQ ID NO: 11 or fragments thereof. Nucleotides of the invention can be synthesized and/or isolated according to methods known in the art.

The invention also relates to a functional expression cassette that allows expression of a polynucleotide according to the invention and including the latter, as well as a vector into which said expression cassette is integrated, and a eucaryotic or procaryotic cell system, that includes an expression cassette or a vector as presented above.

DETAILED DESCRIPTION OF PREFERRED EMBODIMENTS

EXAMPLE 1

Selection of a Phage Clone Coding a Hexapeptide Capable of Reacting Specifically with an Anti-C33 Monoclonal Antibody Screening of a hexapeptide expression bank constructed in the phage according to the method described by Scott and Smith (1990, Science, 249, 386–390) by a specific monoclonal antibody of the C33 antigen of the NS3 region of the hepatitis C virus (anti-C33 monoclonal antibody noted 70-13, No. MO40018Y, available from Anogen) allowed a hexapeptide with the peptide sequence Lys-Phe-Ser-Ser-Arg-Leu SEQ ID NO: 10 to be identified. The immune response of the phage clone carrying this hexapeptide was tested by ELISA, having regard first to the antibody enabling the selection and second to eleven other anti-C33 monoclonal antibodies obtained by the Applicant, and a control monoclonal antibody E1E7 which is specific to the P30 antigen of *Toxoplasma gondii*. The ELISA assays were done as follows: 100 μl of M13 anti-phage antibodies (available from Prim, Inc., Boulder Colo. 80303) diluted 1/500 in a 0.1 M NaHCO$_3$ solution, pH 8.6, were fixed in the wells of Nunc maxisorb (trade name) microtitration plates. After two washings with 0.05% TBS/Tween, 100 μl of purified phage preparation were then incubated for two hours at 37° C. in the wells to fix the phages in the wells. The specific sites were saturated with TBS containing 1%f BSA (bovine serum albumen) for two hours at 37° C. After three washings with 0.05% TBS (50 mM Tris, pH 7.5, 150 mM, NaCl)/Tween 100 μl of anti-C33 monoclonal antibody (Anogen) were added and incubated overnight at 4° C.

After four washings with 0.05% TBS/Tween, 100 μl of anti-mouse conjugate labeled with peroxidase (available from Jackson Immuno Research Laboratories, Inc.) were added, then incubated for one hour at 37° C. The enzyme reaction for developing was carried out by adding 100 μl of an H$_2$O$_2$/orthophenylenediamine (OPD) solution and incubating the sample for 30 minutes at room temperature. The staining reaction was stopped by adding 50 μl 1.8 N sulfuric acid. The optical density was measured on a Bio Mérieux plate reader at 492 nm.

The results show that several monoclonal antibodies tested recognize the selected phage clone carrying the hexapeptide Lys-Phe-Ser-Ser-Arg-Leu (SEQ ID NO: 10). The control response with the anti-P30 antibody was negative. For each of the monoclonal antibodies tested, it was also verified that no reaction was observed between these antibodies and a control phage clone in which no peptide was cloned.

EXAMPLE 2

Inhibition by Recombinant C33 Protein of the ELISA Response Obtained with the Phage Clone Identified An ELISA inhibition assay was performed to determine whether the response obtained with the phage clone identified is inhibited by preincubation of the anti-C33 monoclonal antibody 70-13 with a recombinant C33 protein.

The recombinant C33 protein used in this example was obtained by specific amplification (PCR) (polymerase chain reaction) of the RNA, corresponding to the NS3 region of the hepatitis C virus from the serum of a patient with hepatitis C (genotype 1a). The NS3 gene amplified in this manner was cloned in the pMH expression vector [Cheynet V. et al., (1993) Protein Expression and Purification, 4, 367–372]. The C33 protein is expressed in the form of a fusion protein corresponding to the deduced sequence 1192–1457 of amino acids in the HCV genome [Choo, Q. L., (1989) Science, 244, 359–362] with six histidines at the N-terminal position. The synthesized recombinant C33 protein was purified by affinity chromatography on a metal-chelate column (Ni-NTA resin from Quiagen).

The ELISA assay is carried out as described in Example 1, with the following modifications: the monoclonal antibody 70-13 (20 nM) is preincubated with different concentrations of recombinant C33 protein for 45 minutes at 37° C., then the mixture is added to wells in an ELISA plate in which the phases corresponding to the Lys-Phe-Ser-Ser-Arg-Leu hexapeptide are fixed. The plate is incubated for two hours at 37° C.

The results obtained show that the ELISA response is 33% inhibited by a 30 μg/ml concentration of recombinant C33 protein. This decrease in immunoenzymatic response clearly shows that the phage clone identified is recognized by the same antibodies capable of recognizing the recombinant protein C33.

EXAMPLE 3

Specificity of Human Anti-HCV Antibodies for the Identified Phage Clone having the Sequence Lys-Phe-Ser-Ser-Arg-Leu (SEQ ID NO: 10)

Several of the monoclonal antibodies tested recognize an immunodominant site on the C33 protein and on the phage clone containing the Lys-Phe-Ser-Ser-Arg-Leu hexapeptide. An attempt was made to discover whether this same phage clone is also recognized by the human antibodies present in the serum of patients infected by hepatitis C virus.

The ELISA test is performed under competition conditions in two steps: first, the phage clone to be tested is placed in contact with a fraction of anti-HCV human antibodies and, second, with a monoclonal antibody whose reactivity to said clone is known. Tests are performed with different dilutions of the fraction of human anti-HCV antibody and with a constant quantity of monoclonal antibody. If the human antibodies are capable of recognizing the phage clone tested, inhibition of the binding of the monoclonal antibody to said clone should be observed for decreasing dilution factors.

The "human antibody" fraction is made up of a mixture of five sera from patients infected by HCV. The presence of anti-C33 antibodies in the fraction has been verified with recombinant C33 protein. The monoclonal antibody 12A1H2 (Bio Mérieux) is chosen for the second step, because this antibody is the one showing the greatest reactivity to the phage clone studied in the reactions carried out in Example 1.

100 μl of the various dilutions of said serum mixture are placed in contact with the identified phage clone that is immobilized as described in Example 1, for 45 minutes at 37° C. After two washings with 0.05% TBS/Tween, 100 μl of monoclonal antibody 12A1H2, at the concentration of 50 nM, are added and incubated overnight at 4° C. After four washings with TBS/Tween, 100 μl of the peroxidase-labeled anti-mouse conjugate are added and incubated for one hour at 37° C. Developing is effected by adding 100 μl of a solution of H$_2$O$_2$/orthophenylenediamine (OPD) and incubating the sample For 30 minutes at room temperature. The color reaction is stopped by adding 50 μl of 1.8 N sulfuric acid. Optical density is measured on a Bio Mérieux plate reader at 492 nm. Also, a control was carried out under the same reaction conditions, but with a mixture of human sera not infected with HCV (negative sera) to test the specificity of any reaction between the phage clone tested and the mixture of hepatitis C(+) human sera. Also, a test was conducted in which the reactivity of the mixture of seropositive sera was tested, under the same experimental conditions, with regard to unmodified phage M13.

The results indicate that, for a 1/100 dilution of the mixture of human sera, Inhibition of binding of the monoclonal antibody 12A1H2 is observed to be 40%, and for a 1/10 dilution, the inhibition is approximately 60% This example shows that the phage clone containing the Lys-Phe-Ser-Ser-Arg-Leu sequence is indeed recognized by antibodies present in the sera of patients infected with HCV, and that these antibodies compete with the anti-C33 monoclonal antibody 12A1H2 for binding to said phage clone.

EXAMPLE 4

Multiple Synthesis of Overlapping Hexapeptides and Immunologic Analysis of Said Peptides The above examples illustrate studies conducted on a given hexapeptide, cloned in a more-complex phage structure. The attempt was made to see whether this same peptide sequence, as such, could retain its immunologic properties, with regard in particular to monoclonal antibodies 70-13 (available from Anogen) and 12A1H12 (Bio Mérieux), particularly with regard to the mixture of human sera used in Example 3.

For this study, to determine whether any role is played by the amino acids specific to the phage sequence, which are contiguous to the hexapeptide sequence identified in the clone isolated from the expression bank (see Example 1), a series of overlapping octapeptides covering the sequence Tyr-Ser-His-Ser-Ala-Asp-Gly-Ala-[Lys-Phe-Ser-Ser-Arg-Leu]-Gly-Ala-Ala-Gly-Ala-Glu-Thr-Val-Glu-Ser-Cys-Leu (SEQ ID NO: 12) was synthesized.

The overlapping octapeptides synthesized and analyzed by the Spotscan technique are, in order:

Tyr-Ser-His-Ser-Ala-Asp-Gly-Ala SEQ ID NO: 13
Ser-His-Ser-Ala-Asp-Gly-Ala-Lys SEQ ID NO: 14
His-Ser-Ala-Asp-Gly-Ala-Lys-Phe SEQ ID NO: 15
Ser-Ala-Asp-Gly-Ala-Lys-Phe-Ser SEQ ID NO: 16
Ala-Asp-Gly-Ala-Lys-Phe-Ser-Ser SEQ ID NO: 17
Asp-Gly-Ala-Lys-Phe-Ser-Ser-Arg SEQ ID NO: 18
Gly-Ala-Lys-Phe-Ser-Ser-Arg-Leu SEQ ID NO: 19
Ala-Lys-Phe-Ser-Ser-Arg-Leu-Gly SEQ ID NO: 20
Lys-Phe-Ser-Ser-Arg-Leu-Gly-Ala SEQ ID NO: 21
Phe-Ser-Ser-Arg-Leu-Gly-Ala-Ala SEQ ID NO: 22
Ser-Ser-Arg-Leu-Gly-Ala-Ala-Gly SEQ ID NO: 23
Ser-Arg-Leu-Gly-Ala-Ala-Gly-Ala SEQ ID NO: 24
Arg-Leu-Gly-Ala-Ala-Gly-Ala-Glu SEQ ID NO: 25
Leu-Gly-Ala-Ala-Gly-Ala-Glu-Thr SEQ ID NO: 26
Gly-Ala-Ala-Gly-Ala-Glu-Thr-Val SEQ ID NO: 27
Ala-Ala-Gly-Ala-Glu-Thr-Val-Glu SEQ ID NO: 28
Ala-Gly-Ala-Glu-Thr-Val-Glu-Ser SEQ ID NO: 29
Gly-Ala-Glu-Thr-Val-Glu-Ser-Cys SEQ ID NO: 30
Ala-Glu-Thr-Val-Glu-Ser-Cys-Leu SEQ ID NO: 31

The synthesis was conducted on an activated cellulose membrane according to the technique developed by Berg et al. (1989, J. Ann. Chem. Soc., 111, 8024–8026) and available from Cambridge Research Biochemicals (trade name Spotscan). This technique allows simultaneous synthesis of a large number of peptides. The escerified amino acids used in the synthesis have an α-amino group protected by an FMOC group (Nova Biochem) and side groups protected by protective groups such as, for example, trityl, t-butyl ester, or t-butyl ether. The esterified amino acids are dissolved in N-methylpyrrolidone (NMP) at the concentration of 300 nM and 0.9 µl are deposited at the attachment sites of bromphenol blue. After 15 minutes incubation, amino acids are deposited once again, followed by a further incubation of 15 minutes. If the coupling between the two amino acids is done correctly, a color change is observed (transition from blue to yellow-green). After three washings in DMF, an acetylation step is performed by acetic anhydride. Then the terminal amino groups of the peptides undergoing synthesis are deprotected by piperidine in a 20% solution in DMF. The deposition sites are re-stained by a 1% bromophenol blue solution in DMF, washed three times with methanol, and dried. This sequence of operations constitutes one amino acid addition cycle, and this cycle is repeated until synthesis is complete. When all the amino acids have been added, the NH$_2$ terminal group of the last amino acid is deprotected by piperidine in a 20% solution in DMF and acetylated with acetic anhydride. The protective groups of the side chain are removed by a mixture of dichloromethane/trifluoroacetic acid/triisobutylsilane (5 ml/5 ml/250 µl). The immunoreactivity of the peptides thus synthesized can then be tested, for example, by ELISA.

After synthesis of the various octapeptides, the cellulose membrane is rinsed with methanol, washed in TBS (0.1 M Tris, pH 7.2) then incubated overnight at room temperature in saturation buffer (available from Cambridge Research Biochemicals). After several washings with TBS-T (0.1 M Tris, pH 7.2–0.05% Tween 20), the membrane is placed in contact with a solution of anti-C33 70-13 or 12A1H2 monoclonal antibodies (100 nM), and incubated for four hours at room temperature. After three washings with TBS-T, the anti-mouse-immunoglobulin conjugate labeled with β-galactosidase (available from Cambridge Research Biochemicals) is added to a 1/200 dilution and these materials are incubated for two hours at room temperature. After several washings of the membrane with 0.05% TBS-Tween and PBS, the immunoreactivity at the various spots is developed by adding a solution of substrate (5-bromo-4-chloro-3-indoyl-β-D-galactopyranoside in PBS containing magnesium chloride and potassium ferricyanide) and incubating for ten to forty minutes. The color of the spots is estimated qualitatively on a numerical scale from 0 to 5.

Sequential analysis of the results obtained shows that a first color is obtained with the Asp-Gly-Ala-Lys-Phe-Ser-Ser-Arg sequence. Then, the blue color increases gradually as one progresses through the Tyr-Ser-His-Ser-Ala-Asp-Gly-Ala-[Lys-Phe-Ser-Ser-Arg-Leu]-Gly-Ala-Ala-Gly-Ala-Glu-Thr-Val-Glu-Ser-Cys-Leu sequence to reach a maximum with the Lys-Phe-Ser-Ser-Arg-Leu-Gly-Ala and Phe-Ser-Ser-Arg-Leu-Gly-Ala-Ala sequences. A very slight coloration is still visible for the Ser-Arg-Leu-Gly-Ala-Ala-Gly-Ala sequence which disappears completely starting at the Arg-Leu-Gly-Ala-Ala-Gly-Ala-Glu sequence.

The immunoreactivity of the various peptides synthesized chemically on a cellulose membrane was then tested with the mixture of human sera used in Example 3. The results obtained will a 1/50 dilution of this mixture and a 1/200 dilution of the anti-human-immunoglobulin conjugate labeled with β-galactosidase (available from Cambridge Research Biochemicals) shows a maximum color for the Phe-Ser-Ser-Arg-Leu-Gly-Ala-Ala peptide.

EXAMPLE 5

Substitutions of Amino Acids in the Lys-Phe-Ser-Ser-Arg-Leu-Gly-Ala Peptide aid Immunologic Analysis of Said Modified Peptides In order to determine the degree to which the nature of the various amino acids constituting the Lys-Phe-Ser-Ser-Arg-Leu-Gly-Ala peptide can vary without reducing the antigenic properties of said peptide with respect to anti-C33 antibodies, point substitution tests were performed.

The peptides were synthesized by the method described in the previous example, known as "Spotscan", substituting each amino acid on the peptide at a given position by the other nineteen. These peptides were then tested as described above. The size of each residue can thus be examined and the peptide grouping the best amino acids in each position can then be synthesized. The results obtained show that:

when Arginine in position 5 is replaced by Glycine or Proline or Tyrosine, a better response is observed, Phenylalanine in position 2 can be replaced by Tyrosine: an equivalent response is then observed, in the case of double substitution, Phenylalanine in position 2 can advantageously be replaced by Alanine or Histidine if the amino acid in position 5 is a Tyrosine.

These results are thus obtained with the following sequences:

Lys Phe Ser Ser Gly Leu Gly Ala SEQ ID NO: 32
Lys Phe Ser Ser Pro Leu Gly Ala SEQ ID NO: 33
Lys Phe Ser Ser Tyr Leu Gly Ala SEQ ID NO: 34
Lys Tyr Ser Ser Arg Leu Gly Ala SEQ ID NO: 35
Lys Ala Ser Ser Tyr Leu Gly Ala SEQ ID NO: 36
Lys His Ser Ser Tyr Leu Gly Ala SEQ ID NO: 37

The references cited in this application provide materials illustrative of certain terms and concepts relating to the instant application. These references are hereby totally incorporated by reference.

While the invention has been described with reference to particular preferred embodiments, the invention is not limited to the specific examples given, and other embodiments and modifications can be made by those skilled in the art without departing from the spirit and scope of the invention.

What is claimed is:

1. An isolated or purified polypeptide consisting of the polypeptide sequence defined by SEQ ID NO: 38 or 39.

2. A polypeptide of claim 1, wherein said polypeptide consists of SEQ ID NO: 38.

3. A reagent for detection of Hepatitis C virus infection, comprising a reactive substance comprising at least one polypeptide according to claim 1, wherein said polypeptide is linked to a carrier molecule, a tracer molecule, or a solid substrate, and wherein the carrier molecule, tracer molecule, or solid substrate is unreactive with anti-C33 antibodies.

4. A detection kit for Hepatitis C Virus infection, comprising a reagent according to claim 3, fixed on a solid substrate that is immunologically compatible with said reagent.

5. A reagent according to claim 3, wherein said polypeptide is labelled.

6. A process for assaying C33 antigen in a sample of biological fluid by a competition technique, said process comprising:
   simultaneously placing said sample in contact with a predetermined quantity of anti-C33 antibodies and a predetermined quantity of the reagent according to claim 3;
   measuring a quantity of immune complex thus formed between the reagent and said anti-C33 antibodies; and
   determining a quantity of C33 antigen in said sample by reference to the measured quantity of immune complex.

7. A process for assaying C33 antigen in a sample of biological fluid, comprising:
   placing said sample in contact with a predetermined quantity of anti-C33 antibody;
   adding a predetermined quantity of a reagent according to claim 3;
   measuring a quantity of immune complex thus formed between the reagent and said anti-C33 antibody; and
   determining a quantity of C33 antigen in said sample by reference to the measured quantity of immune complex.

8. A process for separating or purifying antibodies directed against the C33 protein of HCV, comprising contacting a biological sample containing said antibodies with a reagent according to claim 3, and separating out antibodies bound to said reagent.

9. A process for detecting or assaying antibodies directed against the C33 protein of HCV, in a sample suspected of containing such antibodies, comprising contacting said biological sample with a reagent according to claim 3 under conditions permitting formation of immune complexes, and detecting and/or quantifying any immune complex thus formed.

10. A process for detecting or assaying HCV C33 antigen in a biological sample, comprising contacting said sample with a reagent according to claim 3 under conditions permitting formation of immune complexes, and detecting and/or quantifying any immune complex thus formed.

11. An isolated or purified polypeptide, wherein said polypeptide consists of a peptide sequence selected from the group consisting of: SEQ ID NO: 1, 3, 4, 5, 6, 7, 9, 10, 12, 19, 20, 21, 32, 33, 34, 35, 36, and 37.

12. A polypeptide according to claim 11, wherein said polypeptide consists of SEQ ID NO: 10.

13. A reagent for detection of Hepatitis C Virus infection comprising a reactive substance comprising at least one polypeptide according to claim 11, wherein said polypeptide is linked to a carrier molecule, a tracer molecule, or a solid substrate, and wherein the carrier molecule, tracer molecule, or solid substrate is unreactive with anti-C33 antibodies.

14. A detection kit for Hepatitis C Virus infection, comprising a reagent according to claim 13, fixed on a solid substrate that is immunologically compatible with said reagent.

15. A process for assaying C33 antigen in a sample of biological fluid, comprising:
   placing said sample in contact with a predetermined quantity of anti-C33 antibody;
   adding a predetermined quantity of a reagent according to claim 13;
   measuring a quantity of immune complex thus formed between the reagent and said anti-C33 antibody; and
   determining a quantity of C33 antigen in said sample by reference to the measured quantity of immune complex.

16. A process for separating or purifying antibodies directed against the C33 protein of HCV, comprising contacting a biological sample containing said antibodies with a reagent according to claim 13, and separating out antibodies bound to said reagent.

17. A process for detecting or assaying antibodies directed against the C33 protein of HCV, in a sample suspected of containing such antibodies, comprising contacting said biological sample with a reagent according to claim 13 under conditions permitting formation of immune complexes, and detecting and/or quantifying any immune complex thus formed.

18. A process for detecting or assaying HCV C33 antigen in a biological sample, comprising contacting said sample with a reagent according to claim 13 under conditions permitting formation of immune complexes, and detecting and/or quantifying any immune complex thus formed.

19. A process for assaying C33 antigen in a sample of biological fluid by competition technique, said process comprising:
   simultaneously placing said sample in contact with a predetermined quantity of anti-C33 antibodies and a predetermined quantity of the reagent according to claim 13;
   measuring a quantity of immune complex thus formed between the reagent and said anti-C33 antibodies; and
   determining a quantity of C33 antigen in said sample by reference to the measured quantity of immune complex.

* * * * *

UNITED STATES PATENT AND TRADEMARK OFFICE
CERTIFICATE OF CORRECTION

PATENT NO. : 5,985,541
DATED : November 16, 1999
INVENTOR(S) : Colette JOLIVET-REYNAUD It is certified that error appears in the above-indentified patent and that said Letters Patent is hereby corrected as shown below:

On the cover page, in the Assignee information, change "Marcy L'eoile, France" to --Marcy L'Etoile, France--.

Signed and Sealed this

Eighth Day of August, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (v) FRAGMENT TYPE: N-terminal or C-terminal or
            internal (xi) SEQUENCE DESCRIPTION: SEQ ID NO:1:

Asp Gly Ala Lys Phe Ser Ser Arg Leu Gly Ala Ala Gly Ala
1               5                   10

(2) INFORMATION FOR SEQ ID NO:2:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO:2:

Asp Gly Ala Lys Phe Ser Ser Arg
1               5

(2) INFORMATION FOR SEQ ID NO:3:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 3:

Gly Ala Lys Phe Ser Ser Arg Leu
1               5

(2) INFORMATION FOR SEQ ID NO: 4:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 4:

Ala Lys Phe Ser Ser Arg Leu Gly
 1               5

(2) INFORMATION FOR SEQ ID NO: 5:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 5:

Lys Phe Ser Ser Arg Leu Gly Ala
 1               5

(2) INFORMATION FOR SEQ ID NO: 6:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 6:

Phe Ser Ser Arg Leu Gly Ala Ala
 1               5

(2) INFORMATION FOR SEQ ID NO: 7:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 7:

Ser Ser Arg Leu Gly Ala Ala Gly
 1               5

(2) INFORMATION FOR SEQ ID NO: 8:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 8:

Ser Arg Leu Gly Ala Ala Gly Ala
 1               5

(2) INFORMATION FOR SEQ ID NO: 9:

(i) SEQUENCE CHARACTERISTICS:

(A) LENGTH: 8 amino acids
       (B) TYPE: amino acid
       (D) TOPOLOGY: unknown (ii) MOLECULE TYPE: peptide (v) FRAGMENT TYPE: N-terminal or C-terminal or internal (ix) FEATURE:
       (B) LOCATION:2..5
       (D) OTHER INFORMATION: /note= Xaa at position 2
           is = Tyr or Phe or Ala or His; Xaa at position 5
           is = Arg or Gly or Pro or Tyr (xi) SEQUENCE DESCRIPTION: SEQ ID NO: 9:

Lys Xaa Ser Ser Xaa Leu Gly Ala
 1               5

(2) INFORMATION FOR SEQ ID NO: 10:

(i) SEQUENCE CHARACTERISTICS:
       (A) LENGTH: 6 amino acids
       (B) TYPE: amino acid
       (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 10:

Lys Phe Ser Ser Arg Leu
 1               5

(2) INFORMATION FOR SEQ ID NO: 11:

(i) SEQUENCE CHARACTERISTICS:
       (A) LENGTH: 42
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 11:

GAYGGNGCNA ARTTYTCNTC NCGNCTNGGN GCNGCNGGNG CN                    42

(2) INFORMATION FOR SEQ ID NO: 12:

(i) SEQUENCE CHARACTERISTICS:
       (A) LENGTH: 26 amino acids
       (B) TYPE: amino acid
       (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 12:

Tyr Ser His Ser Ala Asp Gly Ala Lys Phe Ser Ser Arg Leu Gly
 1               5                  10                  15

Ala Ala Gly Ala Glu Thr Val Glu Ser Cys Leu
                20                  25

(2) INFORMATION FOR SEQ ID NO: 13:

(i) SEQUENCE CHARACTERISTICS:
       (A) LENGTH: 8 amino acids
       (B) TYPE: amino acid
       (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 13:

Tyr Ser His Ser Ala Asp Gly Ala
1               5

(2) INFORMATION FOR SEQ ID NO: 14:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 14:

Ser His Ser Ala Asp Gly Ala Lys
1               5

(2) INFORMATION FOR SEQ ID NO: 15:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 15:

His Ser Ala Asp Gly Ala Lys Phe
1               5

(2) INFORMATION FOR SEQ ID NO: 16:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 16:

Ser Ala Asp Gly Ala Lys Phe Ser
1               5

(2) INFORMATION FOR SEQ ID NO: 17:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 17:

Ala Asp Gly Ala Lys Phe Ser Ser
1               5

(2) INFORMATION FOR SEQ ID NO: 18:

(i) SEQUENCE CHARACTERISTICS:

```
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 18:

Asp Gly Ala Lys Phe Ser Ser Arg
1               5

(2) INFORMATION FOR SEQ ID NO: 19:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 19:

Gly Ala Lys Phe Ser Ser Arg Leu
1               5

(2) INFORMATION FOR SEQ ID NO: 20:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 20:

Ala Lys Phe Ser Ser Arg Leu Gly
1               5

(2) INFORMATION FOR SEQ ID NO: 21:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 21:

Lys Phe Ser Ser Arg Leu Gly Ala
1               5

(2) INFORMATION FOR SEQ ID NO: 22:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 22:

Phe Ser Ser Arg Leu Gly Ala Ala
1               5
```

(2) INFORMATION FOR SEQ ID NO: 23:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 23:

Ser Ser Arg Leu Gly Ala Ala Gly
 1               5

(2) INFORMATION FOR SEQ ID NO: 24:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 24:

Ser Arg Leu Gly Ala Ala Gly Ala
 1               5

(2) INFORMATION FOR SEQ ID NO: 25:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 25:

Arg Leu Gly Ala Ala Gly Ala Glu
 1               5

(2) INFORMATION FOR SEQ ID NO: 26:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 26:

Leu Gly Ala Ala Gly Ala Glu Thr
 1               5

(2) INFORMATION FOR SEQ ID NO: 27:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 27:

Gly Ala Ala Gly Ala Glu Thr Val
1               5

(2) INFORMATION FOR SEQ ID NO: 28:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 28:

Ala Ala Gly Ala Glu Thr Val Glu
1               5

(2) INFORMATION FOR SEQ ID NO: 29:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 29:

Ala Gly Ala Glu Thr Val Glu Ser
1               5

(2) INFORMATION FOR SEQ ID NO: 30:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 30:

Gly Ala Glu Thr Val Glu Ser Cys
1               5

(2) INFORMATION FOR SEQ ID NO: 31:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 31:

Ala Glu Thr Val Glu Ser Cys Leu
1               5

(2) INFORMATION FOR SEQ ID NO: 32:

(i) SEQUENCE CHARACTERISTICS:
        (A) LENGTH: 8 amino acids
        (B) TYPE: amino acid (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 32:

Lys Phe Ser Ser Gly Leu Gly Ala
 1               5

(2) INFORMATION FOR SEQ ID NO: 33:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 33:

Lys Phe Ser Ser Pro Leu Gly Ala
 1               5

(2) INFORMATION FOR SEQ ID NO: 34:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 34:

Lys Phe Ser Ser Tyr Leu Gly Ala
 1               5

(2) INFORMATION FOR SEQ ID NO: 35:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 35:

Lys Tyr Ser Ser Arg Leu Gly Ala
 1               5

(2) INFORMATION FOR SEQ ID NO: 36:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 36:

Lys Ala Ser Ser Tyr Leu Gly Ala
 1               5

```
(2) INFORMATION FOR SEQ ID NO: 37:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (xi) SEQUENCE DESCRIPTION: SEQ ID NO: 37:

Lys His Ser Ser Tyr Leu Gly Ala
1               5

(2) INFORMATION FOR SEQ ID NO: 38:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (v) FRAGMENT TYPE: N-terminal or C-terminal or internal (ix) FEATURE:
        (B) LOCATION:2..5..7
        (D) OTHER INFORMATION: /note= Xaa at position 2
            is = Tyr or Phe or Ala or His; Xaa at position 5
            is = Arg or Gly or Pro or Tyr;  Xaa at position 7
            is = Gly (xi) SEQUENCE DESCRIPTION: SEQ ID NO: 38:

Lys Xaa Ser Ser Xaa Leu Xaa
1               5

(2) INFORMATION FOR SEQ ID NO: 39:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: N-terminal or C-terminal or internal (ix) FEATURE:
        (B) LOCATION:2..5..7..8
        (D) OTHER INFORMATION: /note= Xaa at position 2
            is = Tyr or Phe or Ala or His; Xaa at position 5
            is = Arg or Gly or Pro or Tyr;  Xaa at position 7
            is = Gly;  Xaa at position 8 is = Ala (xi) SEQUENCE DESCRIPTION: SEQ ID NO: 39:

Lys Xaa Ser Ser Xaa Leu Xaa Xaa
1               5

(2) INFORMATION FOR SEQ ID NO: 40:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (v) FRAGMENT TYPE: N-terminal or C-terminal or internal (ix) FEATURE:
        (B) LOCATION:2..5
        (D) OTHER INFORMATION: /note= Xaa at position 2
            is = Tyr or Phe or Ala or His; Xaa at position 5
```

-continued

```
          is = Arg or Gly or Pro or Tyr (xi) SEQUENCE DESCRIPTION: SEQ ID NO: 40:

Lys Xaa Ser Ser Xaa Leu
1               5
```